United States Patent [19]
Holt et al.

[11] Patent Number: 5,233,992
[45] Date of Patent: Aug. 10, 1993

[54] MRI METHOD FOR HIGH LIVER IRON MEASUREMENT USING MAGNETIC SUSCEPTIBILITY INDUCED FIELD DISTORTIONS

[75] Inventors: Randall W. Holt, Cleveland; Pedro J. Diaz, South Euclid; Errol M. Bellon, Shaker Heights; Gary M. Brittenham, Euclid, all of Ohio

[73] Assignee: Edison Biotechnology Center, Cleveland, Ohio

[21] Appl. No.: 733,309

[22] Filed: Jul. 22, 1991

[51] Int. Cl.$^5$ .............................................. A61B 5/055
[52] U.S. Cl. .............................. 128/653.2; 128/653.5; 324/308; 324/321
[58] Field of Search ........................ 128/653.2–653.5; 324/306–309, 312, 318, 321

[56] References Cited

U.S. PATENT DOCUMENTS

| | | | |
|---|---|---|---|
| 4,849,210 | 7/1989 | Widder | 128/653.4 X |
| 5,055,791 | 8/1991 | Le Roux et al. | 324/309 X |
| 5,071,602 | 12/1991 | Nambu et al. | 324/307 X |

*Primary Examiner*—Francis Jaworski
*Attorney, Agent, or Firm*—Fay, Sharpe, Beall, Fagan, Minnich & McKee

[57] ABSTRACT

A subject (22), such as a human patient, is positioned with a region of interest (24), such as the liver, close proximity to a phantom (12). A Volume image through the liver, the phantom, and adjacent portions of the subject are collected (40) with a magnetic resonance scanner. The phase component of the magnetic resonance data is reconstructed (50) into a three-dimensional phase map. An actually measured field map $H_m(\vec{r})$ is determined (42) from the phase map. A geometric model of the volumes occupied by the liver, the phantom, and adjacent portions of the subject are defined mathematically (44). A calculation routine (46) calculates a calculated or estimated field map $H_c(\vec{r})$ of the distortions to the magnetic field in the phantom which would be caused by the model. A least squares fit routine (48) (i) compares the calculated field map and the measured field map, (ii) based on the difference adjusts a susceptibility of material in the region of interest as defined in the model, and (iii) recalculates the field map. This fitting procedure is iteratively repeated until a susceptibility is determined for the region of interest which predicts the actually measured field map. This susceptibility is proportional to iron concentration.

16 Claims, 2 Drawing Sheets

MRI METHOD FOR HIGH LIVER IRON MEASUREMENT USING MAGNETIC SUSCEPTIBILITY INDUCED FIELD DISTORTIONS

BACKGROUND OF THE INVENTION

The present invention relates to the diagnostic arts. It finds particular application in conjunction with determining iron concentration in the liver of human patients and will be described with particular reference thereto. However, it is to be appreciated that the present invention will also find application in determining the presence of ferrous or other ions which affect magnetic susceptibility in other human tissues, as well as in non-human subjects.

Previously, liver iron levels have been quantized in MRI scanners by correlating susceptibility altered $T_2$ decay with iron levels in the liver. For a liver with normal iron levels, i.e. about 10 μg/ml, the $T_{2^\cdot}$ relaxation time is about 40–50 msec. The $T_{2^\cdot}$ relaxation time becomes shorter with increasing iron levels. In extreme cases, where the iron concentration is on the order of 150 μg/ml, the $T_{2^\cdot}$ relaxation time becomes less than 2 msec. Commercial MRI scanners typically have a spin echo minimum time of about 6 msec. This reduces the signal strength by about 95% and introduces an error or variance of about 50% into the measurement of the $T_{2^\cdot}$ relaxation time.

Outside of the MRI environment, liver iron levels have been measured using SQUID technology. A water bath is disposed between the patient's liver and a SQUID pick-up coil to provide a zero reference. The SQUID coil monitors the actual magnetic field from the liver itself. The relationship between the strength of the liver generated magnetic field and the liver iron concentration have been determined experimentally. When examining a patient, this relationship is consulted to convert the monitored magnetic field strength into a liver iron concentration value.

The present invention contemplates a new and improved technique for measuring liver iron concentration, particularly higher concentrations, in an MRI environment.

SUMMARY OF THE INVENTION

In accordance with one aspect of the present invention, a combined phantom and patient support is provided. A patient support surface which is adapted to extend substantially the entire length of a patient to be examined and to support the patient thereon holds a phantom which has a high proton density, e.g. water.

In accordance with another aspect of the present invention, a region of interest of a subject is positioned contiguous to a phantom. The phantom, the region of interest, and adjacent portions of the subject are immersed in a magnetic field. An image representation or map indicative of magnetic field flux through the phantom is generated. A magnetic susceptibility of the region of interest which results in the measured magnetic field map is determined. The determined magnetic susceptibility of the region of interest is converted into an indication of iron concentration.

In accordance with a more limited aspect of the present invention, the step of determining the magnetic susceptibility of the region of interest includes creating a model of at least the phantom, the region of interest, and the adjacent portions of the subject. An estimate of a field map of the magnetic flux through the phantom is calculated mathematically based on the geometric model with an estimated susceptibility in the region of interest. The estimated field map through the phantom is compared with the measured field map. In accordance with the difference, the estimate of the susceptibility in the region of interest is revised. The steps are repeated until the estimated and measured field maps match within a preselected tolerance.

In accordance with another more limited aspect of the present invention, the step of creating the geometric model includes generating a volume image of the phantom, the region of interest, and adjacent portions of the subject. A volume region occupied by each of the phantom, the region of interest, and adjacent subject portions are defined. The step of calculating the estimated field map includes assigning magnetic susceptibilities to each of the volume regions. Distortions to a uniform magnetic flux attributable to the susceptibilities in each of the volume regions is calculated and the distortions summed.

In accordance with a yet more limited aspect of the present invention, the subject is a human patient and the region of interest the patient's liver. The patient and phantom are immersed in the magnetic field by positioning the patient and phantom within the bore of a magnetic resonance scanner. The step of measuring the magnetic flux through the phantom includes generating a phase map from phase components of acquired magnetic resonance data.

In accordance with a yet more limited aspect of the present invention, a surface coil is mounted contiguous to the phantom. The surface coil is used to receive the magnetic resonance signals whose phase components are used to generate the phase map.

One advantage of the present invention is that it accurately measures high iron concentrations in a magnetic resonance environment.

The present invention accurately measures iron concentrations which are too high to be measured by using $T_{2^\cdot}$ relaxation times.

Still further advantages of the present invention will become apparent to those of ordinary skill in the art upon reading and understanding the following detailed description.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
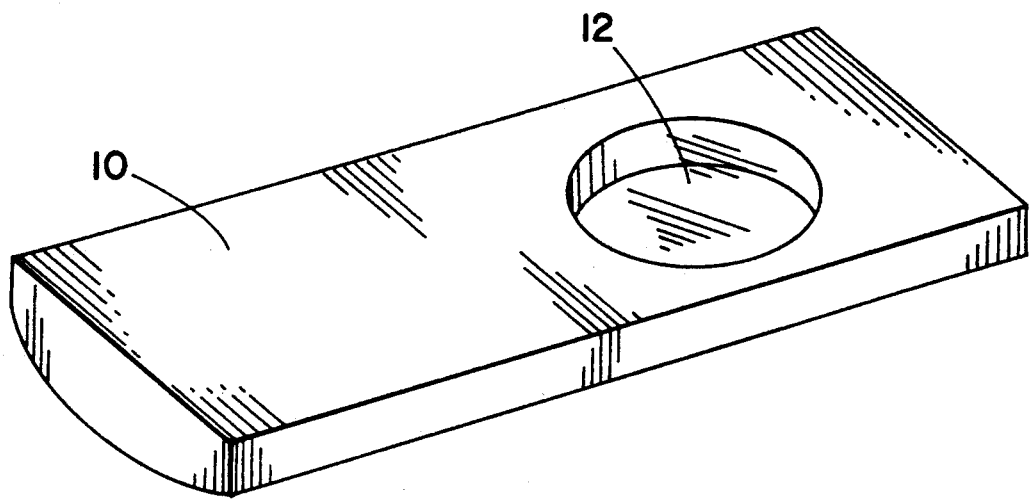
FIG. 1 is a perspective view of a combined patient support couch and phantom in accordance with the present invention.

With reference to FIG. 1, a magnetically inert, ultra low $T_2$ patient support board 10 defines a well for receiving a phantom 12. The patient support 10 is preferably a light weight material such as styrofoam, balsa wood, graphite composite, or the like. In the preferred embodiment, the phantom 12 is a circular plexiglass cylinder that is filled with double distilled water. Other phantoms may also include other high proton density materials, such as aqueous solutions, doped water, low conducting oils, and the like. The phantom is selected to have dimensions commensurate with that of the liver. The phantom is positioned in the support 10 such that the liver of substantially all patients from the smallest to the largest lies over the phantom. Although a circular phantom is illustrated and preferred for its mathematical simplicity, other shapes and sizes of phantoms are also contemplated including, rectangular prisms or slabs, square cylinders, elliptical cylinders, ovoids, amorphous shapes, and the like. Regular geometric shapes are preferred for simplifying the defining of the volume region occupied by the phantom.

Figure 2:
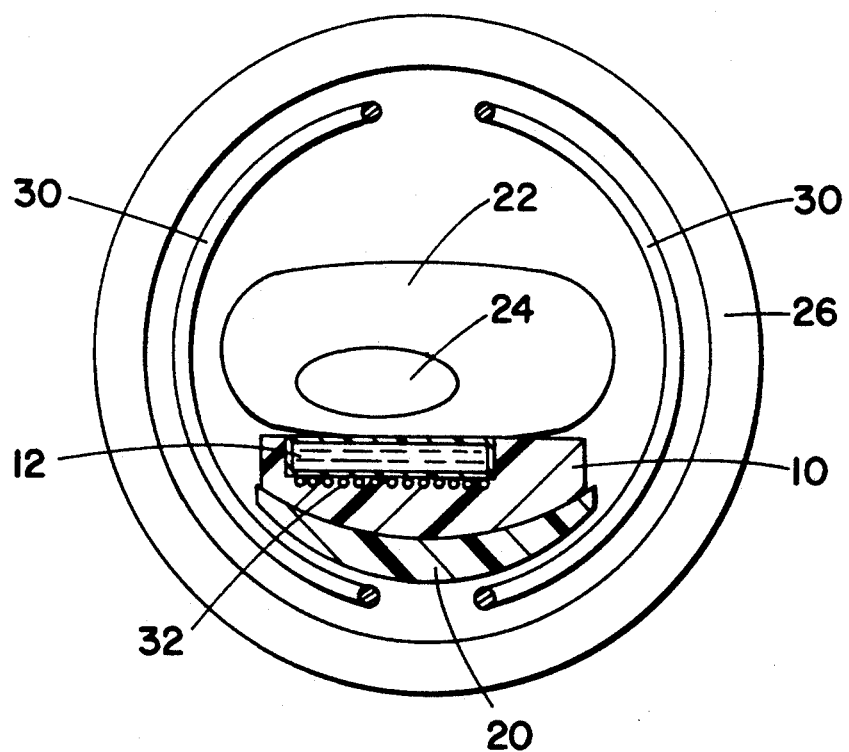
FIG. 2 is a transverse cross-sectional view through the patient support of FIGURE a patient, the patient's liver, and a magnetic resonance imaging scanner; and, FIG. 3 is a diagrammatic illustration showing how the MRI data is processed into a region of interest, e.g. liver, iron concentration information.

With reference to FIG. 2, the patient support 10 and the phantom 12 are supported on a patient couch 20 of an MRI scanner. A patient 22 is supported in the scanner with its liver 24 disposed contiguous to the phantom 12. The patient, patient support, phantom, and patient couch are inserted into a bore of the magnetic resonance scanner defined in part by annular main field magnet 26. The annular magnets generate a strong magnetic field longitudinally through the bore and longitudinally along the patient support, i.e. perpendicular to the plane of FIG. 2. Conventionally, this axis is denoted as the z axis. Of course, magnetic fields in other directions may also be used without departing from the present invention.

The patient and phantom are at least partially surrounded by radio frequency or RF coils 30. As is conventional in MRI scanners, the coils 30 selectively provide pulses of radio frequency energy to induce resonance in dipoles aligned with the z axis magnetic field. The RF coils also transmit RF pulses into the resonating dipoles to manipulate their magnetization vectors for inducing magnetic resonance echoes or performing other magnetic resonance imaging techniques. Magnetic resonance signals generated by resonating the dipoles, particularly during a magnetic resonance echo are detected by the RF coils 30 or a separate surface pick-up coil 32. The use of a localized or surface pick-up coil mounted contiguous to the phantom 12 is preferred in low field applications. The use of the localized coil limits the received magnetic signals to those emanating from an immediately contiguous material, specifically the patient's liver and the phantom.

Figure 3:
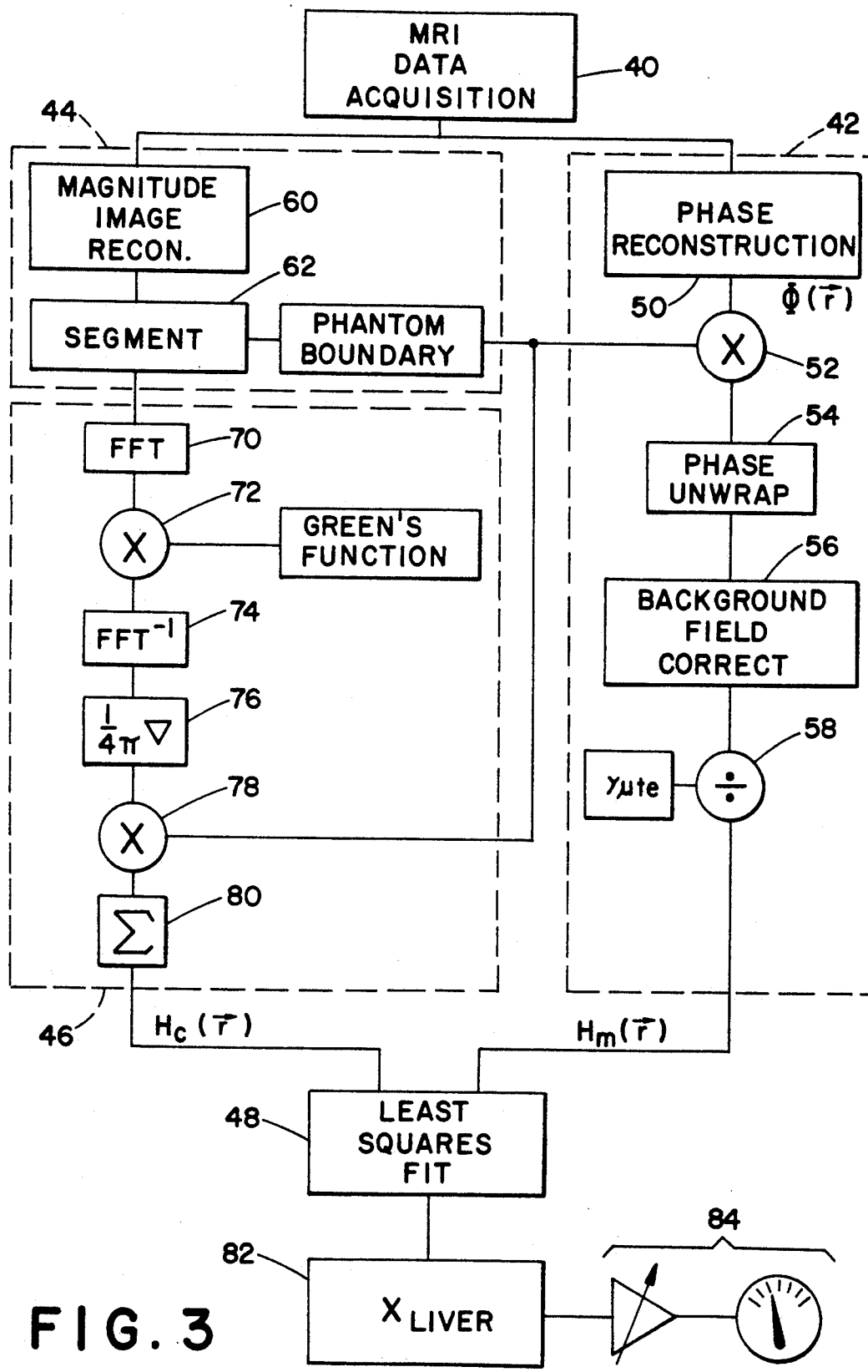

With reference to FIG. 3, a magnetic resonance data acquisition means 40, which is an existing portion of conventional magnetic resonance imaging apparatus, pre-processes, filters, sorts, organizes, and otherwise manipulates the raw resonance data as is conventional in the art. A measured magnetic flux or field map means 42 derives a three-dimensional magnetic field map $H_m(\vec{r})$ that is indicative of the measured magnetic field through the phantom. A geometric modeling means 44 identifies segments or volume regions of the imaged volume which correspond to (i) the phantom, (ii) the liver or region of interest, and (iii) portions of the subject other than the liver or regions of interest and generates a mathematic description of the volume regions. A model magnetic field map calculating means 46 calculates a mathematic model of a field map $H_c(\vec{r})$ through the phantom from the geometric model. A fitting means 48 performs a least squares or other appropriate fitting algorithm which compares the measured magnetic field map from means 42 with the estimated or calculated magnetic field map from 46. The fitting means adjusts an estimated value of the magnetic susceptability in the liver volume region $X_{liver}$ and causes the calculated field map to be recalculated. This process is repeated until the calculated and measured field maps match to within acceptable tolerances.

The measured field map means 42 includes a conventional phase reconstruction means 50 which reconstructs the phase component of the acquired magnetic resonance data into a three-dimensional or volume phase map $\Phi(\vec{r})$. Phase map reconstruction is conventional and is commonly performed with the software in commercially available in MRI scanners. The phase map from Maxwell's equations, is know to be proportional to the field map $H(\vec{r})$:

$$\Phi(\vec{r}) = \gamma \mu \Delta H(\vec{r}) t_e \qquad (1),$$

where $\gamma$ is the gyromagnetic ratio, $\mu$ is the permeability, and $t_e$ is the echo time. Thus, for a given echo time, the distortion $\Delta H_m(\vec{r})$ from the uniform magnetic field is readily obtained from the phase map $\Phi(\vec{r})$.

An editing means 52 edits or deletes the volume phase map to eliminate data which does not correspond to the magnetic field map in phantom. Phase data commonly overlays itself with a $2\pi$ periodicity. This $2\pi$ overlay is corrected or unwrapped by a conventional technique known as phase unwrapping, which is performed by a phase unwrapping step or means 54. A background magnetic field means 56 corrects the unwrapped phase map data for background magnetic fields. More specifically, a field map is measured with means 42 in the presence of the phantom but in the absence of the subject. This provides an indication of the background magnetic field, or more particularly the phase map, when it is undistorted by the presence of a patient's liver. A proportionality factor adjusting means 58 adjusts the background adjusted phase map for the gyromagnetic ration and permeability of the phantom and the echo time of Equation (1). The step or means 58 adjusts the phase map for these and other system proportionality factors to generate the measured field map $H_m(\vec{r})$.

The geometric modeling means 44 includes a reconstruction means 60 for generating a magnitude volume image representation, i.e. a conventional MRI image. More specifically to the preferred embodiment, the reconstruction means 60 generates a series of transverse planes through the liver, the adjacent torso, and the phantom. An operator marks the boundaries of he phantom, liver or other region of interest, and the torso on each slice. A segmentation means 62 defines mathematically the boundary or volume of the phantom, the region of interest, and the subject. The definition of the volume of the phantom is used by editing means 52. This generates a mathematic model of the patient.

From Maxwell's equations, one can calculate the field map $H_c(\vec{r})$ that will result when the liver or other of the mathematically defined volume regions of the geometric model has different values. More specifically, $$H_c(\vec{r}) = H_0(\vec{r}) - \frac{1}{4\pi} \nabla \cdot \int_{v'} M(\vec{r'}) \cdot \nabla \frac{1}{|\vec{r} - \vec{r'}|} d^3 r', \qquad (2)$$

where $H_0(\vec{r})$ is the background field and $M(\vec{r})$ is the magnetization vector. Equation (2) is also the integral solution to Laplace's equation. In the present system in which the object is some combination of paramagnetic, diamagnetic, and superparamagnetic materials, and the magnetization vector is linear, then $$\vec{M(r)} = X(\vec{r})\vec{H(r)} = X(\vec{r})H_0 k \qquad (3)$$

where $X_i(\vec{r})$ is the susceptibility. Moreover, the principle of superposition holds. That is, the effect on the magnetization vector or field map from each of the volume regions can be determined independently and summed, i.e.

$$H_c(\vec{r}) = H_0(\vec{r}) - \frac{V}{4\pi} \nabla \cdot \sum_{v'} X(\vec{r'})H_0(\vec{r'}) \cdot \frac{\vec{r} - \vec{r'}}{|r - r'|^3}. \qquad (4)$$

For a constant magnetic field, i.e. $H_0(\vec{r}) = H_0$, and recognizing that the dot product is a three-dimensional Fourier convolution, Equation (4) becomes:

$$H_c(\vec{r}) = H_0(\vec{r}) + \frac{H_0}{4\pi} \nabla \cdot \left[ X(\vec{r}) * \left( \frac{z}{|\vec{r}|^3} \right) \right], \qquad (5)$$

where * denotes the convolution operation and $z/|\vec{r}|^3$ is Green's function.

The model field map calculating means 46 includes means for performing the Fourier convolution function. More specifically, a Fourier transform means 70 Fourier transforms the susceptibility data which is multiplied by means 72 with Green's function. An inverse Fourier transform means 74 transforms this data from Fourier space back to image space. A volume operator and weighting means 76 weights the convolved data and operates on it with a volume operator. In the present model in which the magnetic resonance image or uniform magnetic field extends along the z axis, and in which susceptibility are assumed to be uniform within each volume region along the x and y axes, the volume operator reduces to the first derivative with respect to the z axis. An editing means 78 edits the portion of the calculated field map which does not correspond to the phantom. A summing means 80 sums the contribution from each volume region to produce the calculated magnetic field map $H_c(\vec{r})$. More specifically, for each voxel value of the three-dimensional phase map or corresponding volume image, the contribution to the calculated field map is determined and summed. More specifically to the preferred embodiment, the system calculates the contribution of the liver region, the phantom region, and the torso region independently. While calculating the contribution from any one of these regions, the system steps through each pixel and operates on the retrieved value with a function $V_i(\vec{r})$ which assumes the value of "1" if the voxel is within the selected volume region and "0" when the voxel is outside of the selected volume region. In this manner, after the background field is removed, Equation (5) reduces to:

$$H_c(r) = k \sum_i X_i \frac{d}{d_3} \left( V_i(r) * \frac{z}{|\vec{r}|^3} \right). \qquad (6)$$

In this manner, the algorithm means 46 calculates the estimated or calculated field map $H_c(\vec{r})$ from the geometric model for the phantom. The phase means 42 generates an actually measured field map $H_m(\vec{r})$ for the phantom. The least squares fit means compares the measured and calculated field maps. The least squares fit means iteratively adjusts the susceptibility $X_{liver}$ of Equation (6) for i=liver in accordance with the variance between $H_c(\vec{r})$ and $H_m(\vec{r})$. The calculated phase map is recalculated for the re-estimated liver susceptibility. Note that the phantom and torso contributions to the calculated field map do not need to be recalculated. Based on the difference between the estimated and actual phase map, the contribution attributable to the susceptibility of the liver is again adjusted and the procedure repeated. The least squares or other fitting technique is repeated until the susceptibility of the liver is determined within acceptable tolerances. An output means 82 outputs the calculated susceptibility of the liver. A conversion means 84 converts the susceptibility of the liver to a iron or ferrous ion concentration. Because this relationship is substantially linear, the conversion means preferably multiplies the liver susceptibility by a preselected constant. Alternately, a look up table may be generated from clinical data to convert the liver susceptibility more accurately to the iron concentration.

It is to be appreciated, that more than three regions of the subject may be defined by the geometric modeling means 44. In the human liver analyzing embodiment, ferrous iron concentrations might also be found in regions of bone marrow. These regions with distinct susceptibilities from the rest of the subject may be defined as a fourth region. Similarly, other regions of the phase and magnitude imaged volume which have differing susceptibilities may be defined until each volume region has substantially the same susceptibility. Further, the invention is also applicable to the measurement of iron concentration in other organs or portions of the body, such as the bone marrow referenced above. Further, this technique can be used in non-human subjects to detect and quantify iron concentrations in selected regions of the non-human subject.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of measuring iron concentration in a selected volume region of a subject, the method comprising:

positioning the subject with the selected volume region contiguous to a phantom;

subjecting the phantom, the selected volume region, and at least portions of the subject adjacent the volume region to a magnetic field;

measuring a measured magnetic field map indicative of magnetic field distortion through the phantom, when the phantom is contiguous to the volume region;

determining a magnetic susceptibility of the volume region which results in the measured magnetic field map.

2. The method as set forth in claim 1 wherein the step of determining the magnetic susceptibility of the selected volume region includes:

a) creating a geometric model of at least the phantom, the selected volume region, and the adjacent portions of the subject;

b) calculating a calculated magnetic field map through the phantom with an estimated susceptibility in the selected volume region;

c) comparing the calculated magnetic field map with the measured magnetic field map;

d) revising the estimated selected volume region susceptibility in accordance with the comparison;

e) repeating steps (b)–(d) until the calculated field map and the measured field map match within preselected tolerances.

3. The method as set forth in claim 2 wherein the step of creating the model includes:

generating a volume image of the phantom, the selected volume region, and the adjacent portions of the patient;

defining a phantom volume region occupied by the phantom and a subject volume region occupied by portions of the subject adjacent the selected volume region.

4. The method as set forth in claim 3 wherein the calculated field map calculating step includes:

assigning susceptibilities to the volume regions;

calculating distortions to the field map attributable to each volume region;

summing the calculated distortions.

5. The method as set forth in claim 4 wherein in the susceptibility assigning step, a uniform susceptability is assigned in each volume region.

6. The method as set forth in claim 1 wherein the step of subjecting the phantom, selected volume region, and adjacent portions of the subject to the magnetic field includes positioning the subject and phantom within a magnetic field of a magnetic resonance scanner and wherein the step of generating the measured field map includes acquiring magnetic resonance signals and reconstructing a phase map from phase components of the magnetic resonance signals.

7. The method as set forth in claim 6 wherein the magnetic resonance signal acquiring step includes receiving magnetic resonance signals with a surface coil disposed contiguous to the phantom.

8. A method of measuring liver iron concentrations, the method comprising:

positioning a patient's liver contiguous to a phantom;

subjecting the phantom, liver, and adjacent portions of the patient to a magnetic field;

measuring a magnetic field map of a magnetic field through the phantom;

determining a magnetic susceptibility of the liver which results in the measured magnetic field map;

converting the magnetic susceptibility into an indication of liver iron concentration.

9. A apparatus for determining iron concentration in combination with a magnetic resonance imaging scanner, the iron concentration determining apparatus comprising:

a phantom disposable in the magnetic resonance imaging scanner in close association with a selected portion of a subject within which the iron concentration is to be determined;

a magnetic resonance data acquisition means for acquiring magnetic resonance data from a volume which includes at least a portion of the subject, the phantom, and the selected subject portion;

a means for generating from the acquired magnetic resonance data a field map indicative of distortion of a magnetic field through the phantom;

a means for determining a susceptibility of the selected subject portion which causes the measured field map.

10. The apparatus set forth in claim 9 wherein the susceptibility determining means includes:

a means for calculating a calculated field map indicative of distortions caused by a selectable susceptibility of the selected subject portion;

a fitting means for adjusting the susceptibility of the selected subject portion until the calculated field map substantially matches the measured field map.

11. The apparatus as set forth in claim 10 wherein the calculated field map calculating means includes:

a modeling means for generating a geometric model which identifies a phantom volume region corresponding to the phantom, a selected volume region corresponding to the selected portion of the subject, and a subject volume region corresponding to other regions of the subject;

a means for summing distortions caused by each of the volume regions.

12. The apparatus as set forth in claim 11 wherein the calculated field map calculating means further includes:

a convolver means for convolving the selected susceptibility with Green's function;

a weighting means for weighting the Green's function convolved susceptibility.

13. The apparatus as set forth in claim 12 wherein the measured field map generating means includes:

a phase reconstruction means for reconstructing a volume phase map from the acquired magnetic resonance data;

an editing means for editing the phase map to a region corresponding to the phantom;

a means for phase unwrapping the phase map.

14. The apparatus as set forth in claim 9 wherein the measured field map generating means includes:

a phase reconstruction means for reconstructing a volume phase map from the acquired magnetic resonance data;

an editing means for editing the phase map to a region corresponding to the phantom;

a means for phase unwrapping the phase map.

15. The apparatus as set forth in claim 9 wherein the phantom includes a volume of water.

16. The apparatus as set forth in claim 9 wherein the magnetic resonance data acquiring means includes a surface coil mounted contiguous to the phantom.

* * * * *